United States Patent [19]

Tackett

[11] Patent Number: 5,412,581
[45] Date of Patent: May 2, 1995

[54] METHOD FOR MEASURING PHYSICAL PROPERTIES OF HYDROCARBONS

[75] Inventor: James E. Tackett, Littleton, Colo.

[73] Assignee: Marathon Oil Company, Findlay, Ohio

[21] Appl. No.: 971,886

[22] Filed: Nov. 5, 1992

[51] Int. Cl.⁶ .................. G01N 21/35; G01N 21/25; G01J 2/42
[52] U.S. Cl. .................... 364/498; 364/497; 364/499; 250/343; 250/345; 250/349; 250/339.01
[58] Field of Search .......... 250/343, 339, 345, 349, 250/339.01; 364/498, 497, 499

[56] References Cited

U.S. PATENT DOCUMENTS

| | | | |
|---|---|---|---|
| 3,896,312 | 7/1975 | Brown et al. | 250/343 |
| 4,184,074 | 1/1980 | Blunck | 250/345 |
| 4,800,279 | 1/1989 | Hieftje et al. | 250/339 |
| 4,891,519 | 1/1990 | Nohira et al. | 250/349 |
| 4,963,745 | 10/1990 | Maggard | 250/343 |
| 5,003,175 | 3/1991 | Fabinski et al. | 250/345 |
| 5,023,804 | 5/1992 | Hoult | 364/498 |
| 5,121,337 | 6/1992 | Brown | 364/498 |
| 5,145,785 | 9/1992 | Maggard et al. | 436/8 |
| 5,206,701 | 4/1993 | Taylor et al. | 356/325 |
| 5,223,715 | 6/1993 | Taylor | 250/343 |
| 5,225,679 | 7/1993 | Clarke et al. | 250/343 |
| 5,308,982 | 10/1993 | Ivaldi et al. | 250/339.01 |
| 5,349,188 | 9/1994 | Maggard | 250/339 |
| 5,349,189 | 9/1994 | Maggard | 250/339.07 |
| 5,362,965 | 11/1994 | Maggard | 250/339.12 |

FOREIGN PATENT DOCUMENTS

WO91/15762 10/1991 WIPO .......... G01N 33/28

OTHER PUBLICATIONS

Foulk, S. J. and Catalano, V. J., "Determination of Octane Number Using Remote Sensing NIR Spectroscopy", *American Laboratory*, Nov. 1989, pp. 78–81.

Kelly, J. J. et al., "Prediction of Gasoline Octane Numbers from Near-Infrared Spectral Features in the Range 660-1215 nm", *Analytical Chemistry*, Feb. 1989, pp. 313–320.

Swarin, S. J. and Drumm, C. A., "Predicting Gasoline Properties Using Near-IR Spectroscopy", *Spectroscopy*, Sep. 1992, pp. 42–49.

Primary Examiner—Emanuel T. Voeltz
Assistant Examiner—Patrick J. Assovad
Attorney, Agent, or Firm—Jack L. Hummel; Jack E. Ebel

[57] ABSTRACT

A system for measuring the physical characteristics of a hydrocarbon places a reference hydrocarbon cell in thermal contact with a sample cell containing an unknown hydrocarbon. A near infrared spectrum measurement is taken of both the cells. Measurement data from the sample cell is adjusted by the measurement data from the reference cell, and the adjusted measurement data is evaluated by a model to predict the characteristics of the sample. The model is built from a teaching set of hydrocarbons having known physical characteristics and the reference hydrocarbon. Each of the teaching set hydrocarbons is measured and then adjusted by a measurement of the same reference hydrocarbon, and the adjusted measurements are used to build the model.

21 Claims, 7 Drawing Sheets

METHOD FOR MEASURING PHYSICAL PROPERTIES OF HYDROCARBONS

FIELD OF THE INVENTION

This invention relates to evaluation of the physical properties of samples and more particularly to methods employing near infrared spectrometry to quantify physical properties. Even more particularly, the invention relates to compensation of near infrared spectrometry measurements used for the prediction of physical properties of hydrocarbons.

BACKGROUND OF THE INVENTION

The need often arises for rapid, accurate, and continuous measurement of the physical properties of hydrocarbons, such as octane, gravity, vapor pressure, etc. The antiknock quality of gasoline is one of the physical properties often measured, since it is an important gasoline performance specification. In the laboratory, octane is measured using two single-cylinder variable compression ratio engines: a research octane engine (RON) which operates at lower speed and inlet temperature, and a motor octane engine (MON), which operates at higher speed and higher inlet temperature. The two values obtained from running gasoline through these two engines are averaged to obtain an antiknock index (AKI) that is believed to be closer to the antiknock performance of gasoline in automobiles. When implemented as an online method, this engine octane method of determining the octane of gasoline requires expensive equipment, frequent maintenance, the availability of prototype fuels, and takes about 20 minutes per sample to run.

Near infrared spectrometric analysis has been used to determine indirectly the qualitative properties of various hydrocarbon samples. U.S. Pat. No. 4,800,279, issued Jan. 24, 1989 to Hieftje, et al. entitled "Methods and Devices for Near Infrared Evaluation of Physical Properties of Samples", "Prediction of Gasoline Octane Number from Near Infrared Spectral Features in the Range 660–1215 nm" by Jeffery J. Kelley, et al., Analytical Chemistry, Volume 61, Number 4, Feb. 15, 1989, pp. 31320, and "Predicting Gasoline Properties Using Near-IR spectroscopy" by Stephen J. Swarin and Charlene A. Drumm, Spectroscopy, Volume 7, number 7, Sep. 1992, all describe a method of predicting the antiknock index of gasoline using near infrared spectrometry. These methods described passing energy in the near infrared region of the electromagnetic spectrum through a sample of gasoline and measuring the wavelength of radiation absorbed by the gasoline and the amount of absorption at each wavelength. This measurement results in a spectral profile, or spectrum, which can then be compared to the spectrum of a data set of samples having known antiknock indexes.

A problem can occur, however, with using this method in an online process environment. Because the density of gasoline, or any other sample, will vary with temperature, and because the spectrometer measuring instrument readings may also vary with instrument wear and temperature, the spectrum obtained from measuring a sample under a current set of conditions may not match the spectrum obtained when the sample was measured under the previous set of conditions.

The prior art methods of solving this problem have centered around stabilizing the temperature of the spectrometer and the temperature of the sample being measured. This is difficult, however, in a field site such as a refinery, where gasoline may have been stored and transported to a test cell outside in ambient weather conditions which vary with the time of the year. When the spectrometer is not located adjacent to the sample measuring site, typically a connection is made between the spectrometer and the sample using fiber optics, which introduce other variables.

It is thus apparent that there is a need in the art for an improved method of measuring the absorption of near infrared energy by a hydrocarbon. There is further need in the art for such a method that compensates for temperature fluctuations and other variations in the measurement. The present invention meets these and other needs.

SUMMARY OF THE INVENTION

It is an aspect of the present invention to measure the absorption of near infrared energy by hydrocarbons.

It is another aspect to compensate for temperature and other variations in the measurement.

It is a further aspect to provide such compensation by using a reference hydrocarbon located in proximity to the test hydrocarbon.

The above and other aspects of the invention are accomplished in a system which places a reference cell, containing a reference hydrocarbon, in thermal contact with a sample cell that contains an unknown hydrocarbon. Since these two cells are adjacent and in thermal contact, any changes in the unknown hydrocarbon spectrum will also occur in the reference hydrocarbon spectrum.

Prior to predicting the characteristics of an unknown sample, a set of spectrum measurements is made of the reference hydrocarbon and a selected teaching set of hydrocarbons. Each of the teaching set hydrocarbons is selected to have a different chemical composition. The reference hydrocarbon is repeatedly measured, just prior to measuring each of the teaching set hydrocarbons. Each of the teaching set measurements are adjusted using the reference hydrocarbon measurement taken just prior to the teaching set measurement. The adjusted measurements are then used to build a model used to predict the physical characteristics of an unknown sample. The model is built using multivariate analysis in the same manner as described above with respect to U.S. Pat. No. 4,800,279, the Kelley et al. article, and the Swarin et al. article.

When predicting the characteristics of an unknown sample, a spectrum measurement is taken of both the reference hydrocarbon and the sample hydrocarbon within a very short amount of time. The data from the reference hydrocarbon is used to adjust the sample data in the same manner as the teaching set data was adjusted. The unknown sample adjusted data is then evaluated by the model to predict the physical characteristics.

The measurement adjustment is made by first adjusting the baseline of the spectrum measurements, then measuring the location of the highest peak of the spectrum and the area under the curve of the spectrum of the reference hydrocarbon. The reference peak location, and optionally a constant value, is subtracted from each of the wavelengths of the sample spectrum to shift the sample spectrum wavelength axis to standard conditions. The sample area is divided by the reference area, and optionally also divided by a constant value to adjust the absorption axis to standard conditions. The constant values are used to adjust the spectrum of the teaching and sample hydrocarbons to approximately the same spectrum range as the reference hydrocarbon.

BRIEF DESCRIPTION OF THE DRAWINGS

The above and other aspects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined by referencing the appended claims.

Figure 1:
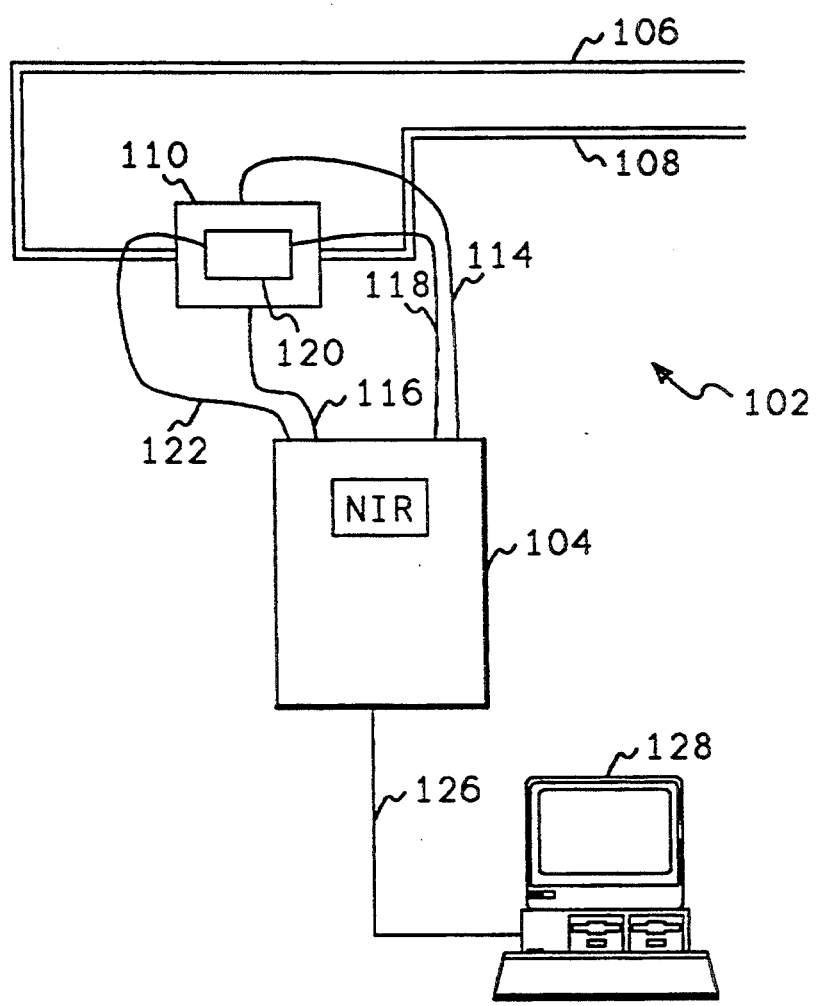
FIG. 1 shows a block diagram of the invention within its environment.

FIG. 1 shows a block diagram of the invention within its environment. Referring now to FIG. 1, a measurement system 102 contains an analyzer module 104, which is a near infrared spectrometer. A sample hydrocarbon to be measured flows in through an inlet pipe 106, through a sample cell 110, and out through an exit pipe 108. The spectrometer 104 may be, for example, a Guided Wave, Inc., model 300 spectrometer, however, other spectrometers that measure the near infrared spectrum could be used. The sample cell 110 may be a "shuttle probe" flowcell designed by Guided Wave, Inc., where the fiber optics attach to each end of a "wand" that has a cell slot in the center. This slot allows a hydrocarbon sample to pass between two lenses that are approximately one centimeter apart. Other cell designs may be used, however.

A fiber optic cable 114 connects the energy output of the spectrum analyzer 104 to one side of the sample cell 110. The other side of the sample cell 110 connects through a fiber optic cable 116 back to a detector within the spectrum analyzer 104 to allow energy that has passed through the sample to return to the detector within the spectrometer 104.

A reference cell 120 containing a reference hydrocarbon is connected to the energy output of the spectrum analyzer 104 through a fiber optic cable 118. The output of the reference cell 120 is connected through a second fiber optic cable 122 to the detector within the spectrum analyzer 104. In this manner the spectrum analyzer 104 is able to take a spectrum measurement of the sample hydrocarbon through the sample cell 110 and also take a measurement of the reference hydrocarbon contained in the reference cell 120. The sample cell 110 and the reference cell 120 are both in physical and thermal contact with each other. In this manner, both the sample cell 110 and the reference cell 120 maintain the same temperature at all times. Also, the fiber optic cables connecting the spectrum analyzer 104 to both the sample cell 110 and the reference cell 120 have the same length and take the same path between the cells and the spectrum analyzer, so that they maintain the same temperature and other conditions.

The sample data taken by the spectrometer 104 is connected through a connection 126 to a computer system 128 where the data is analyzed using multivariate analysis techniques. The software performing this multivariate analysis in the present invention is a commercial multivariate analysis software package called Unscrambler developed by H. Martens, available from CAMO A/S, Trondheim, Norway.

Figure 2:
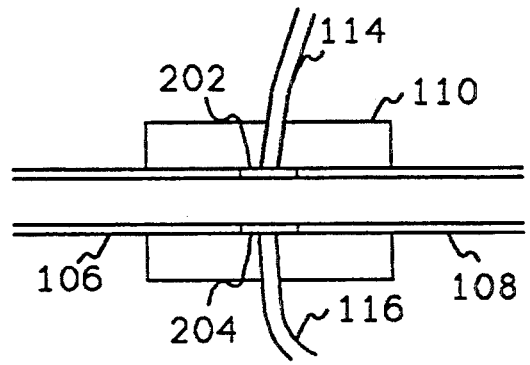
FIG. 2 shows a more detailed block diagram of the sample cell.

FIG. 2 shows a more detailed diagram of the sample cell 110. Referring now to FIG. 2, the sample cell 110 allows the inlet pipe 106 and outlet pipe 108 to pass through the walls of the cell 110. A pair of lenses 202 and 204 are connected between the inlet pipe 106 and the outlet pipe 108. The fiber optics cables 114 and 116 are connected to the lenses 202 and 204 to allow energy to pass through the lenses, and through the hydrocarbon contained within the pipes 106 and 108.

Figure 3:
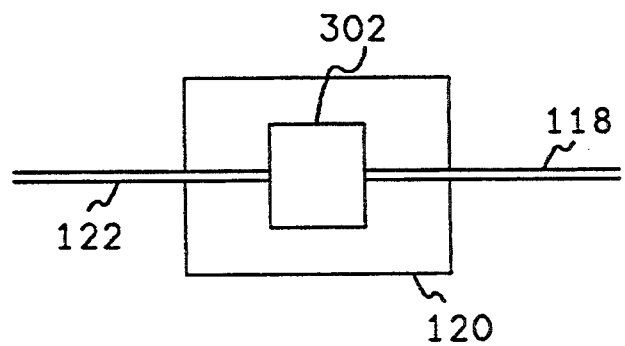
FIG. 3 shows a more detailed block diagram of the reference cell.

FIG. 3 shows a more detailed block diagram of the reference cell 120. Referring now to FIG. 3, the reference cell 120 contains a standard flame sealed 1 cm cuvette 302, although other types of cells may be used. Fiber optics cables 118 and 122 are connected to allow energy from the spectrum analyzer to pass through the reference hydrocarbon in the cell.

Figure 4:
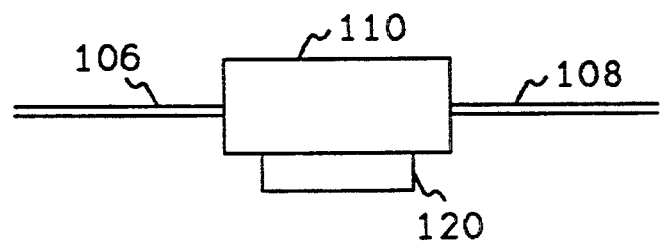
FIG. 4 shows a top view of the cells, illustrating the thermal contact of the cells.

FIG. 4 shows a top view of the sample and reference cells and illustrates the thermal contact of the two cells. Referring now to FIG. 4, the reference cell 120 is shown physically adjacent to the sample cell 110 to provide for thermal contact.

Before taking measurements of unknown hydrocarbon samples, a teaching set of hydrocarbon samples must first be assembled. This teaching set comprises samples of hydrocarbons, each having different chemical compositions and known physical characteristics, such as antiknock index. Spectrometric measurements are taken of these known hydrocarbons. In addition, just prior to each teaching set sample measurement, a measurement is taken of a reference hydrocarbon which will be used in the reference cell 120 (FIG. 1).

The reference hydrocarbon is selected to have a spectrum measurement that resembles the spectrum measurement of the teaching set samples. The present invention uses a highly branched dodecylbenzene as the reference hydrocarbon when measuring the antiknock index of gasoline. The feed stocks used for making dodecylbenzene sulfonates contain a mixture of branch dodecylbenzene isomers that is suitable for the reference hydrocarbon. A 50/50 by volume mixture of P-Cymene and 2-Methylhexane is also suitable for the reference hydrocarbon when measuring the octane of gasoline. These are relatively high boiling compounds that are available in a pure state, so it is not difficult to obtain and maintain them in a sealed reference cell, such as the reference cell 120.

Once the teaching set measurement data and the reference hydrocarbon measurement data have been obtained, and a multivariate calibration model built, the characteristics of an unknown sample hydrocarbon can be predicted. Details of constructing a multivariate calibration model can be found in "Multivariate Calibration", Herald Martens and Tormod Naes, John Wiley & Sons, 1989.

Figure 5:
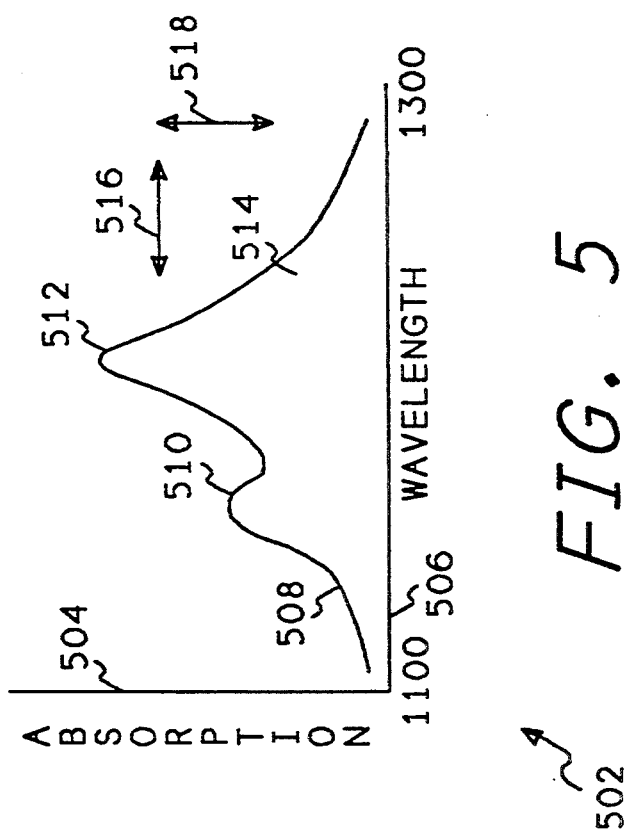
FIG. 5 shows a spectrum chart illustrating the near infrared spectrum of a sample.

FIG. 5 shows an example output of the spectrometer 104 when measuring the absorption of gasoline. The measurement spectrum is in the wavelength of 1100 nanometers to 1300 nanometers. In some applications, other ranges within the near infrared region of 650 to 2000 nanometers could be used. A measurement curve 508 contains a first peak 510 which indicates the presence of aromatics within the sample. A second, higher, peak 512 is the major peak which is used for the peak position measurement. In addition, the area of the pattern 514, underneath the curve, is used for the correction of the area measurement. When temperature changes occur, the curve 508 may shift in either of the directions indicated by arrow 516, which is the wavelength axis, or the curve may shift in either of the directions indicated by arrow 518, which is the absorption axis, or both may occur. Before the peak or area measurements are made, the curve 508 is baseline corrected by adjusting the absorption at 1100 and 1300 nanometers to zero. That is, the curve is shifted upward or downward to cause the curve to be zero at 1100 and 1300 nanometers.

The measurement adjustment method first determines the location of the peak 512 within the reference hydrocarbon spectrum. The system then adjusts the wavelength axis of the teaching set or sample peak, depending upon whether the model is being constructed, or the characteristics of an unknown hydrocarbon are being determined, in either direction indicated by arrow 516, by subtracting the location of the reference hydrocarbon peak. A constant value may also be subtracted from the peak location to define a set of standard conditions. In the present invention, this constant is 1191.76 for a dodecylbenzene reference hydrocarbon. For example, for measuring the antiknock index of gasoline using the present invention, the constant is selected to shift the adjusted spectra of the sample and teaching set hydrocarbons into the range of 1100 to 1300 nanometers.

The system then takes the area 514 under the curve 508 of the reference hydrocarbon. The spectrum of the teaching set or unknown sample is adjusted by dividing it by the area of the reference hydrocarbon measurement. This result may also be divided by a constant to define standard conditions. For example, this constant is 30,025 for a dodecylbenzene reference hydrocarbon in the present invention. This constant is selected in the same manner as the peak constant.

Once the new adjusted peak location and area are determined, sample values are taken for approximately 100 points between 1100 and 1300 nanometers, and these sample values are sent to the multivariate software.

FIGS. 6-9 show the process of the present invention. The software within this process is performed within the computer system 128 to cause spectrometer 104 to take the indicated measurements. The computer system 128 then adjusts the location of the sample peak and the area underneath the sample curve. The exact method of determining the spectrum peak, and the exact method of determining the area underneath the curve, are unimportant. It is only important that all measurements use the same method. So long as the reference hydrocarbon, teaching set and the samples are taken using the same method, the results are dependable.

Figure 6:
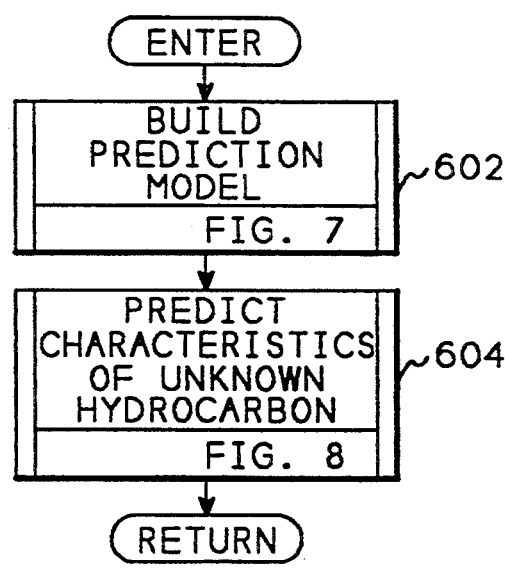
FIG. 6 shows a flowchart of the overall measurement process.
Figure 7:
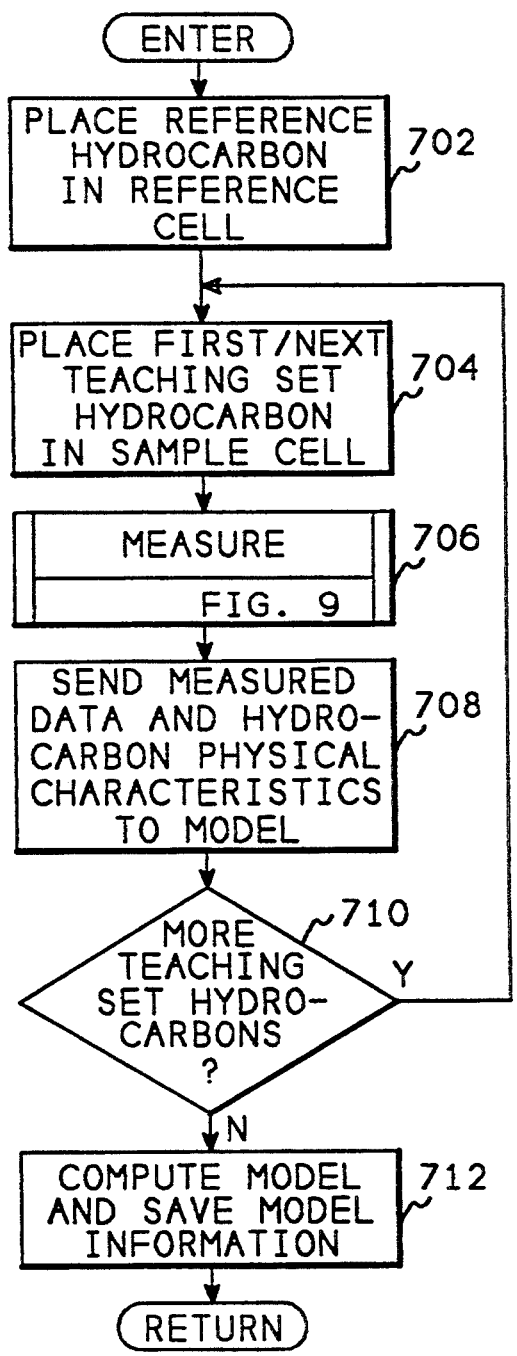
FIG. 7 shows a flowchart of building the model data.
Figure 8:
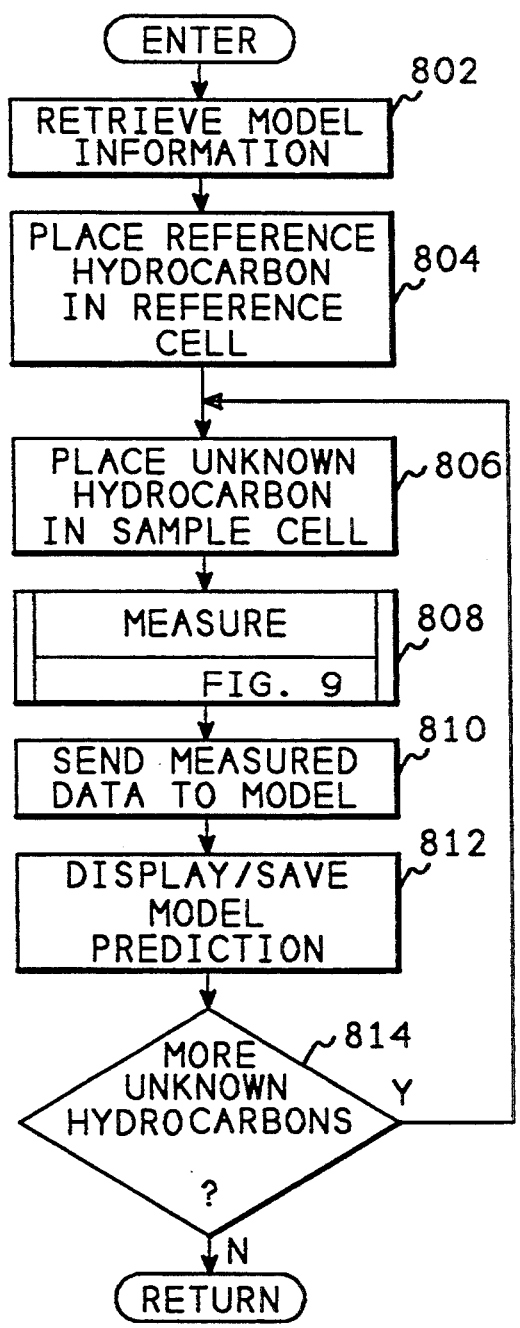
FIG. 8 shows a flowchart of measuring and predicting an unknown sample.

Referring now to FIGS. 6-9, after entry into FIG. 6, block 602 calls FIG. 7 to build the prediction model, and then calls FIG. 8 to predict the physical characteristics of unknown hydrocarbons. Those skilled in the art will recognize that the model can be built at one time and the prediction of unknown hydrocarbons made at a later time, or at many different times for many different unknown hydrocarbons. Typically, the model should have to be built once for a particular test setup, and should only have to be built again if something in the test setup changes, for example, if a different spectrometer is used.

FIG. 7 is called from block 602 of FIG. 6 to build the prediction model data. Referring now to FIG. 7, after entry, block 702 places the reference hydrocarbon into the reference cell. This could be done manually, or automatically. Block 704 then places the first, or next, teaching set hydrocarbon into the sample cell. As with the reference cell, this could be done manually or automatically. As described above, the teaching set contains multiple hydrocarbons with known physical characteristics.

Figure 9:
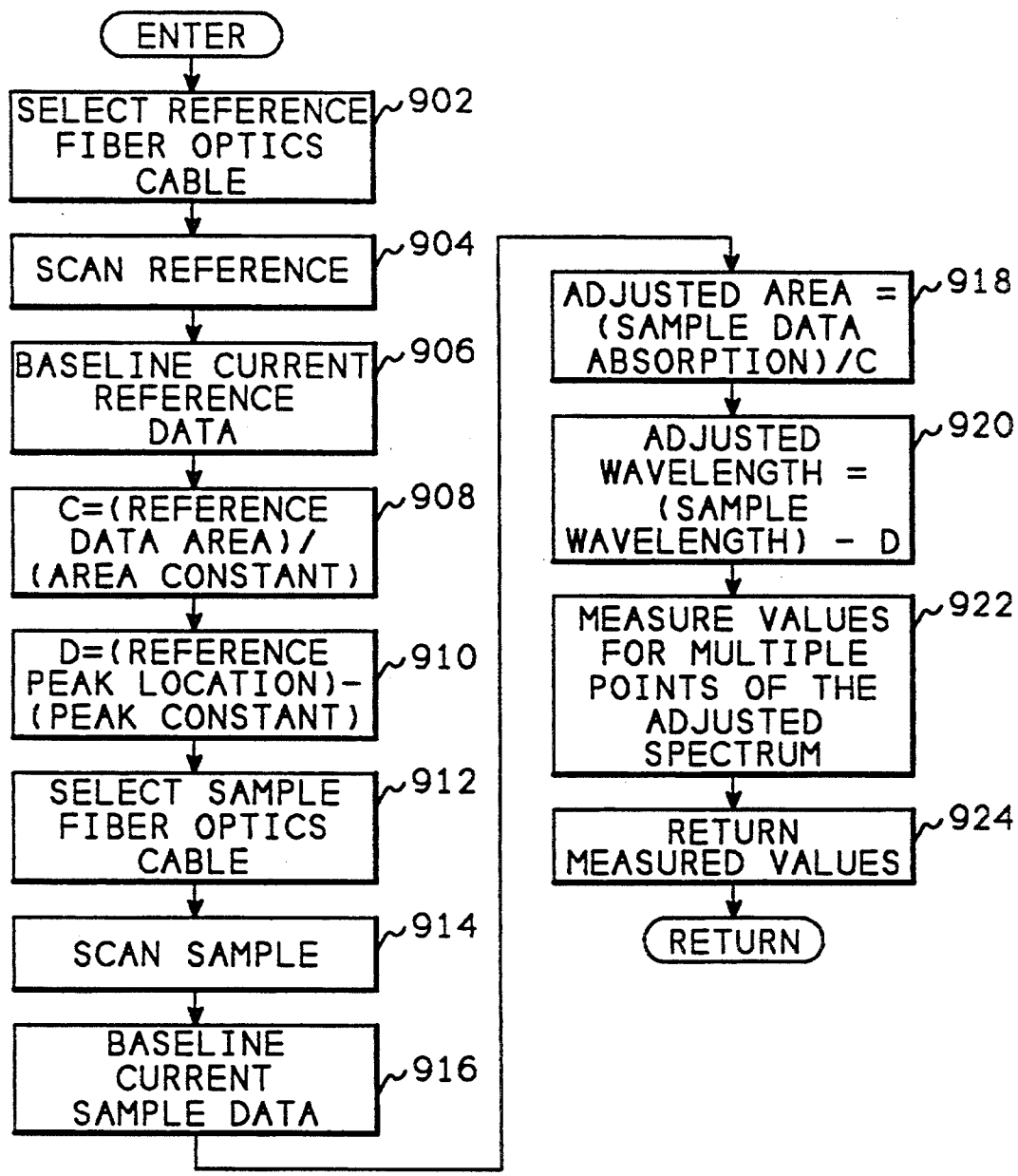
FIG. 9 shows a flowchart of the spectrum measurement and adjustment process.

Block 706 then calls FIG. 9 to take a measurement of the spectrum of both cells and adjust the peak and areas of the measurement as discussed above. Block 708 sends the adjusted measurement data to the multivariate software in the computer system 128 (FIG. 1), and block 710 determines whether additional teaching set hydrocarbons need to be measured. If additional teaching set hydrocarbons do need to be measured, block 710 transfers back to block 704 to measure the next hydrocarbon in the teaching set. After all the teaching set hydrocarbons have been measured and the data sent to the model, block 712 computes the model information and saves the model information for use in predicting the characteristics of an unknown hydrocarbon.

FIG. 8 shows a flowchart of the process of predicting the characteristics of an unknown hydrocarbon sample. Referring now to FIG. 8, after entry, block 802 retrieves the model information and places it into the multivariate program within the computer system 128 (FIG. 1). Block 804 then places the reference hydrocarbon into the reference cell, and block 806 places the unknown hydrocarbon into the sample cell. As discussed above this process may be manual or automatic. As shown in FIG. 1, typically the unknown hydrocarbon flows through the sample cell.

Block 808 then calls FIG. 9 to measure and adjust the measurement data, and block 810 sends the data to the multivariate model which makes the prediction. Block 812 then displays the prediction. Block 812 is typically performed by the multivariate software model in the computer system 128 (FIG. 1).

Block 814 then determines whether additional predictions are to be made, and if so, transfers back to block 806 to make the next prediction. After all predictions have been made, block 814 returns to FIG. 6.

FIG. 9 shows a flowchart of the process for measuring and adjusting the measurement of the hydrocarbons. Referring now to FIG. 9, after entry, block 902 selects the fiber optic cables leading to the reference cell. This is typically done with a multiplexer device within the spectrum analyzer. Block 904 then instructs the spectrum analyzer to take a spectrum measurement of the reference hydrocarbon. Block 906 then corrects the baseline of the spectrum by adjusting the spectrum up or down (in the direction of arrow 518 of FIG. 5) until the sample values at 1100 nanometers and 1300 nanometers are zero. Block 908 computes the value of a variable C by dividing the area of the reference spectrum by a constant, such as the constant described above. Block 910 computes the value of a variable D by subtracting a constant, such as the constant described above, from the peak location of the peak 512 (FIG. 5). As discussed above, the peak location and area are determined by the spectrum analyzer.

Block 912 selects the sample cell fiber optics cable, block 914 scans the hydrocarbon in the sample cell, and Block 916 adjusts the baseline of the sample cell data. Block 918 adjusts the area by dividing each absorption value by the variable C computed above, and block 920 adjusts the wavelength axis by subtracting the variable D computed above. Block 922 measures the values of multiple points of the adjusted spectrum. Typically, values are measured for 100 sample points equally spaced along the spectrum. Block 924 then returns the sample point values.

Having thus described a presently preferred embodiment of the present invention, it will now be appreciated that the aspects of the invention have been fully achieved, and it will be understood by those skilled in the art that many changes in construction and circuitry and widely differing embodiments and applications of the invention will suggest themselves without departing from the spirit and scope of the present invention. The disclosures and the description herein are intended to be illustrative and are not in any sense limiting of the invention, more preferably defined in scope by the following claims.

What is claimed is:

1. A method for determining at least one physical property of a sample hydrocarbon using spectrometry, said method comprising the steps of:
   (a) selecting a reference hydrocarbon;
   (b) selecting a teaching set of hydrocarbons, each having at least one physical property of the at least one physical property to be determined;
   (c) placing said reference hydrocarbon in a reference cell in thermal contact with a sample cell;
   (d) placing one of said hydrocarbons from said teaching set into said sample cell;
   (e) measuring a reference absorption spectrum of said reference hydrocarbon;
   (f) measuring a teaching absorption spectrum of said hydrocarbon within said sample cell wherein a set of wavelengths used for said measuring is the same as a set used in step (e);
   (g) combining said reference absorption spectrum and said teaching absorption spectrum to create a teaching adjusted spectrum;
   (h) computing a plurality of teaching sample values, one for each of a plurality of sample points of said teaching adjusted spectrum;
   (i) inputting each of said teaching sample values into a multivariate analysis system to build a multivariate calibration model;
   (j) repeating steps (d) through (i) for each hydrocarbon in said teaching set;
   (k) placing said reference hydrocarbon in a reference cell in thermal contact with a sample cell containing said unknown-hydrocarbon sample;
   (l) measuring a test reference absorption spectrum of said reference hydrocarbon in said reference cell, wherein a set of wavelengths used for said measuring is the same as a set used in step (e);
   (m) measuring a sample absorption spectrum of said unknown hydrocarbon in said sample cell wherein a set of wavelengths used for said measuring is the same as a set used in step (e);
   (n) combining said test reference absorption spectrum and said sample absorption spectrum to create a test adjusted spectrum;
   (o) computing a plurality of test sample values, one for each of a plurality of sample points of said second adjusted spectrum; and
   (p) inputting each of said test sample values into said multivariate analysis system to compare said test sample values to said multivariate calibration model to determine said at least one physical property of said sample hydrocarbon.

2. The process of claim 1 wherein step (g) comprises the following steps (g1) and (g2) and wherein step (n) comprises the following steps (n1) and (n2):
   (g1) measuring a peak location of said teaching reference spectrum;
   (g2) subtracting said teaching reference absorption spectrum peak location from each wavelength of said teaching absorption spectrum and dividing said reference absorption area into each absorption value of said teaching reference absorption spectrum to create said teaching adjusted spectrum;
   (n1) measuring a peak location and area of said test reference spectrum;
   (n2) subtracting said test reference absorption spectrum peak location from each wavelength of said sample absorption spectrum and dividing said reference absorption area into each absorption value of said teaching reference absorption spectrum to create said test adjusted spectrum.

3. The method of claim 1 wherein each of said measuring steps uses a spectrometer for said measuring and wherein each of said measuring steps further comprises the step of connecting said reference cell and said sample cell to said spectrometer through fiber optics cables prior to said measurement.

4. The method of claim 1 wherein step (e) further comprises the step of selecting at least one set of wavelengths in the near infrared spectrum for said measuring.

5. The method of claim 4 further comprising the step of selecting wavelengths between 1100 nanometers and 1300 nanometers for said measuring.

6. The method of claim 1 wherein each of said teaching set hydrocarbons and said unknown hydrocarbon comprises gasoline.

7. The method of claim 6 wherein said reference hydrocarbon comprises equal parts by volume of p-cymene and 2-methylhexane.

8. The method of claim 6 wherein said reference hydrocarbon comprises a highly branched dodecylbenzene isomer.

9. A method for determining at least one physical property of a sample hydrocarbon using spectrometry, said method comprising the steps of:
   (a) selecting a reference hydrocarbon and placing said reference hydrocarbon in a reference cell adjacent a sample cell;
   (b) selecting a teaching set of hydrocarbons, each having at least one physical property of the at least one physical property to be determined;

(c) selecting one hydrocarbon from said teaching set and placing said selected hydrocarbon in said sample cell;

(d) measuring a reference absorption spectrum of said reference hydrocarbon;

(e) measuring a teaching absorption spectrum of said hydrocarbon in said sample cell, wherein a set of wavelengths used for said measuring is the same as a set used in step (d);

(f) measuring a peak location and area of said reference spectrum;

(g) subtracting said reference absorption spectrum peak location from each wavelength of said teaching absorption spectrum and dividing said reference absorption area into each absorption value of said teaching absorption spectrum to create an adjusted spectrum;

(h) computing a plurality of sample values each sampling one point of said adjusted spectrum;

(i) inputting each of said teaching sample values into a multivariate analysis system to build a multivariate calibration model;

(j) repeating steps (c) through (i) for each hydrocarbon in said teaching set;

(k) placing said reference hydrocarbon in a reference cell in thermal contact with a sample cell containing said unknown hydrocarbon sample; measuring a test reference absorption spectrum of said reference hydrocarbon in said reference cell, wherein a set of wavelengths used for said measuring is the same as a set used in step (d);

(m) measuring a sample absorption spectrum of said unknown hydrocarbon in said sample cell, wherein a set of wavelengths used for said measuring is the same as a set used in step (d);

(n) measuring a peak location and area of said test reference spectrum;

(o) subtracting said test reference absorption spectrum peak location from each wavelength of said unknown hydrocarbon absorption spectrum and dividing said reference absorption area into each absorption value of said unknown hydrocarbon absorption spectrum to create a test adjusted spectrum;

(p) computing a plurality of test sample values each sampling one point of said test adjusted spectrum; and (q) inputting each of said test sample values into said multivariate analysis system to compare said test sample values to said multivariate calibration model to determine said physical properties.

10. The method of claim 9 wherein each of said measuring steps uses a spectrometer for said measuring and wherein each of said measuring steps further comprises the step of connecting said test reference cell and said test sample cell to said spectrometer through fiber optics cables prior to said measurement.

11. The method of claim 9 wherein step (d) further comprises the step of selecting at least one set of wavelengths in the near infrared spectrum for said measuring.

12. The method of claim 11 further comprising the step of selecting wavelengths between 1100 nanometers and 1300 nanometers for said measuring.

13. The method of claim 9 wherein each of said teaching set hydrocarbons and said unknown hydrocarbon comprises gasoline.

14. The method of claim 13 wherein said reference hydrocarbon comprises equal parts by volume of p-cymene and 2-methylhexane.

15. The method of claim 13 wherein said reference hydrocarbon comprises a highly branched dodecylbenzene isomer.

16. A method for determining the antiknock index of a sample gasoline using spectrometry, said method comprising the steps of:

(a) selecting a reference hydrocarbon and placing said reference hydrocarbon in a reference cell adjacent a sample cell;

(b) selecting a teaching set of gasolines, each having an antiknock index within a range of antiknock indexes for said sample gasoline;

(c) selecting one gasoline from said teaching set and placing said selected gasoline in said sample cell;

(d) measuring a reference absorption spectrum of said reference hydrocarbon;

(e) measuring a teaching absorption spectrum of one gasoline within said teaching set, wherein a set of wavelengths used for said measuring is the same as a set used in step (d);

(f) measuring a peak location and area of said reference spectrum;

(g) subtracting said reference absorption spectrum peak location from each wavelength of said teaching absorption spectrum and dividing said reference absorption area into each absorption value of said teaching absorption spectrum to create a teaching adjusted spectrum;

(h) computing a plurality of teaching sample values, one for each of a plurality of sample points of said teaching adjusted spectrum;

(i) inputting each of said sample values into a multivariate analysis system to build a multivariate calibration model;

(j) repeating steps (c) through (i) for each gasoline in said teaching set;

(k) placing said reference hydrocarbon in a reference cell in thermal contact with a sample cell containing said sample gasoline; measuring a test reference absorption spectrum of said reference hydrocarbon in said reference cell, Wherein a set of wavelengths used for said measuring is the same as a set used in step (d);

(m) measuring a sample absorption spectrum of said sample gasoline in said sample cell, wherein a set of wavelengths used for said measuring is the same as a set used in step (d);

(n) measuring a peak location and area of said test reference spectrum;

(o) subtracting said test reference absorption spectrum peak location from each wavelength of said sample absorption spectrum and dividing said reference absorption area into each absorption value of said unknown hydrocarbon absorption spectrum to create a test adjusted spectrum;

(p) computing a plurality of test sample values, one for each of a plurality of sample points of said second adjusted spectrum; and (q) inputting each of said test sample values into said multivariate analysis system to compare said test sample values to said multivariate calibration model to determine said antiknock index.

17. The method of claim 16 wherein each of said measuring steps uses a spectrometer for said measuring and wherein each of said measuring steps further comprises the step of connecting said test reference cell and said test sample cell to said spectrometer through fiber optics cables prior to said measurement.

18. The method of claim 16 wherein step (d) further comprises the step of selecting at least one set of wavelengths in the near infrared spectrum for said measuring.

19. The method of claim 18 further comprising the step of selecting wavelengths between 1100 nanometers and 1300 nanometers for said measuring.

20. The method of claim 19 wherein said reference hydrocarbon comprises equal parts by volume of p-cymene and 2-methylhexane.

21. The method of claim 19 wherein said reference hydrocarbon comprises a highly branched dodecylbenzene isomer.

* * * * *

UNITED STATES PATENT AND TRADEMARK OFFICE
CERTIFICATE OF CORRECTION

PATENT NO. : 5,412,581
DATED : May 2, 1995
INVENTOR(S) : James E. Tackett

It is certified that error appears in the above-indentified patent and that said Letters Patent is hereby corrected as shown below:

Col. 10, line 42:  Delete "measuring a test reference".
Col. 10, line 43:  Insert --(1) measuring a test reference--.
Col. 10, line 44:  Delete "Wherein" and insert --wherein--.

Signed and Sealed this

Fifth Day of September, 1995

Attest:

BRUCE LEHMAN

Attesting Officer    Commissioner of Patents and Trademarks